United States Patent [19]
Adelstein et al.

[11] Patent Number: 5,869,513
[45] Date of Patent: Feb. 9, 1999

[54] 2-[(1H-BENZIMIDAZOL-2-YLSULFINYL) METHYL]BENZENAMINES

[75] Inventors: Gilbert William Adelstein, Evanston; Peter Hadley Jones, Lake Bluff; Chung-Hwai Yen, Prospect Heights, all of Ill.

[73] Assignee: G. D. Searle & Co., Chicago, Ill.

[21] Appl. No.: 737,843

[22] Filed: May 24, 1985

[51] Int. Cl.⁶ .................. A61K 31/415; C07D 235/28
[52] U.S. Cl. .......................... 514/395; 548/307.1
[58] Field of Search .................. 514/395; 548/307.1

[56]  References Cited

U.S. PATENT DOCUMENTS

| | | | |
|---|---|---|---|
| 3,894,037 | 7/1975 | Brenneisen et al. | 548/329 X |
| 4,045,563 | 8/1977 | Berntsson et al. | 548/327 X |
| 4,045,564 | 8/1977 | Berntsson et al. | 546/271 X |
| 4,182,766 | 1/1980 | Krassó et al. | 546/271 X |
| 4,248,880 | 2/1981 | Krassó et al. | 548/181 X |
| 4,255,431 | 3/1981 | Junggren et al. | 546/271 X |
| 4,327,102 | 4/1982 | Crossley | 546/339 X |
| 4,337,257 | 6/1982 | Junggren et al. | 546/271 X |
| 4,359,465 | 11/1982 | Ruwart | 546/271 X |
| 4,394,509 | 7/1983 | Crossley | 546/339 |
| 4,472,409 | 9/1984 | Senn-Bilfinger | 546/271 X |
| 4,594,425 | 6/1986 | Musser et al. | 548/329 X |

FOREIGN PATENT DOCUMENTS

| | | | |
|---|---|---|---|
| 72532 | 2/1983 | European Pat. Off. | 548/329 |
| 1277763 | 12/1984 | European Pat. Off. | 546/271 |
| 130729 | 1/1985 | European Pat. Off. | 546/271 |
| 1509192 | 1/1968 | France | 548/329 |
| 3415971 | 11/1984 | Germany | 546/271 |
| 2134523 | 8/1984 | United Kingdom | 546/271 |
| 2137616 | 10/1984 | United Kingdom | 546/271 |
| 2163747 | 3/1986 | United Kingdom | 548/329 |

OTHER PUBLICATIONS

Derwent Abstract of Belgian Patent 903,128, Dec. 16, 1985.
J.B. Spenney, *J. Clin. Gastro.*, 5 (Suppl. 1), 7–15 (1983).
B. Beilenson, et al., *J. Chem. Soc.*, 98–102 (1942).
B.R. Baker, et al., *J. Org. Chem.*, 17, 141–148 (1952).
B.R. Baker et al., *J. Org. Chem.*, 17, 149–156 (1952).
J. Chandra Rajan, et al., *Anal. Biochem.*, 72, 407–412 (1976).
L. Burrows, et al., *J. Surgical Res.*, 4, 147–150 (1964).

*Primary Examiner*—Laura L. Stockton
*Attorney, Agent, or Firm*—Roger A. Williams

[57] ABSTRACT

This invention relates to 2-[(1H-benzimidazol-2-ylsulfinyl) methyl]benzenamines that are useful in the treatment and prevention of ulcers.

33 Claims, No Drawings

2-[(1H-BENZIMIDAZOL-2-YLSULFINYL) METHYL]BENZENAMINES

BACKGROUND OF THE INVENTION (a) Field of the Invention

This invention relates to compounds that are useful in the treatment and prevention of ulcers. More particularly, this invention relates to 2-[(1H-benzimidazol-2-ylsulfinyl) methyl]benzenamines that inhibit gastric acid secretion and which are, therefore, useful in the treatment of peptic ulcers. The compounds of this invention directly inhibit acid secretion by parietal cells of the stomach through inhibition of $(H^+ + K^+)$-ATPase. For review, see, e.g., J. G. Spenney, "Biochemical Mechanisms of Acid Secretion by Gastric Parietal Cells," *J. Clin. Gastro.*, 5 (Suppl. 1), 7–15 (1983). In addition, some of the compounds of this invention also exert cytoprotective activity. For review of cytoprotection, see, e.g., U.S. Pat. No. 4,359,465.

(b) Prior Art

Heterocyclylalkylsulfinylbenzimidazoles have been disclosed as gastric acid secretion inhibitors. See U.S. Pat. Nos. 4,472,409, 4,394,509, 4,337,257, 4,327,102, 4,255,431, 4,045,564, and 4,045,563; British Patent No. 2,134,523; and German Offenlegungeschrift No. 3,415,971. Some heterocyclylalkylsulfinylbenzimidazoles have also been disclosed as cytoprotective agents. See U.S. Pat. No. 4,359,465. The following structure is illustrative of compounds disclosed in these patents:

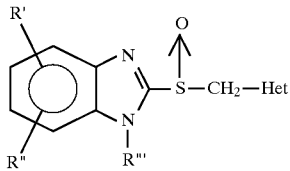

wherein R' and R" represent hydrogen, alkyl, halogen, trifluoromethyl, cyano, carboxy, hydroxy, acyl, and the like; R'" represents hydrogen, alkyl, acyl, alkoxysulfonyl, and the like; and Het represents heterocyclic groups containing at least one endocyclic (ring) nitrogen. No compound disclosed in these patents includes an unsubstituted or substituted phenyl group instead of the Het group nor exocyclic amino or acylamino functions attached to the Het group. In contrast, the compounds of the present invention are distinguished from the prior art by having (optionally substituted amino)phenyl groups instead of a Het group. Thus, the compounds of the present invention are clearly distinguished from the prior art compounds cited.

Heterocyclylalkylsulfinylnaphth[2,3-d]imidazoles have also been disclosed as gastric acid secretion inhibitors. See U.S. Pat. Nos. 4,248,880 and 4,182,766. The compounds disclosed in these patents are related to those illustrated in the above structure, except for having a substituted naphth [2,3-d]imidazole group instead of the benzimidazole group. Similarly, other heterocyclylalkylsulfinylbenzimidazoles having a ring fused to the benzimidazole group have been disclosed as gastric acid secretion inhibitors and cytoprotective agents. See European Patent Application Nos. 130, 729 and 127,763. Because of the additional ring fusions of these compounds, as well as for the same reasons stated in the preceding paragraph, the compounds of the present invention are structurally distinguished from prior art compounds cited.

SUMMARY OF THE INVENTION

The invention relates to compounds of Formula I:

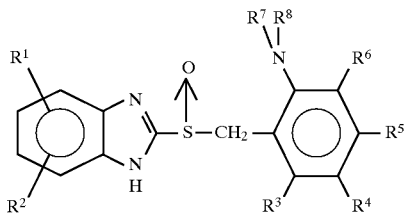

wherein $R^1$ is:
a) hydrogen;
b) alkyl of 1 to 4 carbon atoms, inclusive;
c) alkoxy of 1 to 4 carbon atoms, inclusive; or
d) fluorinated alkyl of 1 to 4 carbon atoms, inclusive;
wherein $R^2$ is:
a) hydrogen;
b) alkyl of 1 to 4 carbon atoms, inclusive;
c) fluorinated alkyl of 1 to 4 carbon atoms, inclusive; or
d) alkoxycarbonyl of 2 to 6 carbon atoms, inclusive;
wherein $R^3$, $R^4$, $R^5$, and $R^6$, each being the same or different, are:
a) hydrogen;
b) alkyl of 1 to 4 carbon atoms, inclusive;
c) alkoxy of 1 to 4 carbon atoms, inclusive;
d) halogen; or
e) fluorinated alkyl of 1 to 4 carbon atoms, inclusive;
wherein $R^7$ is:
a) hydrogen;
b) alkyl of 1 to 4 carbon atoms, inclusive; or
c) alkanoyl of 2 to 6 carbon atoms, inclusive;
wherein $R^8$ is:
a) hydrogen; or
b) alkyl of 1 to 4 carbon atoms, inclusive; or the pharmaceutically acceptable acid addition salts thereof; or the pharmaceutically acceptable base addition salts thereof.

Although the structure shown for Formula I indicates one tautomeric form, it is understood that this representation is for convenience only and that the scope of this invention includes as equivalents all tautomeric forms of the compounds of this invention.

Examples of alkyl of 1 to 4 carbon atoms, inclusive, are methyl, ethyl, propyl, butyl, and the isomeric forms thereof, generally referred to as lower alkyl.

Examples of alkoxy of 1 to 4 carbon atoms, inclusive, are methoxy, ethoxy, propoxy, butoxy, and the isomeric forms thereof.

Examples of fluorinated alkyl of 1 to 4 carbon atoms, inclusive, are fluoromethyl, difluoromethyl, trifluoromethyl, 1- or 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms thereof.

Examples of alkoxycarbonyl of 2 to 6 carbon atoms, inclusive, are methoxycarbonyl, ethoxycarbonyl, propoxycarbonyl, butoxycarbonyl, pentoxycarbonyl, and the isomeric forms thereof.

Examples of alkanoyl of 2 to 6 carbon atoms, inclusive, are acetyl, propanoyl, butanoyl, pentanoyl, hexanoyl, and the isomeric forms thereof.

Examples of halogen are fluorine, chlorine, bromine, and iodine.

Examples of pharmaceutically acceptable acid addition salts include the hydrochloride, hydrobromide, hydroiodide, sulfate, phosphate, acetate, propionate, lactate, maleate, malate, succinate, and tartrate salts.

Examples of pharmaceutically acceptable base addition salts include lithium, sodium, potassium, magnesium, calcium, titanium, ammonium, alkylammomium, dialkylammomium, trialkylammomium, tetraalkylammomium, and guanidinium salts.

DESCRIPTION OF THE INVENTION

The compounds of this invention may be prepared by the methods illustrated in the following Schemes. Unless otherwise specified, the various substituents are defined as for Formula I, above. Scheme A illustrates the preparation of sulfur-containing intermediates of Formula IV.

SCHEME A

Intermediates of Formula IV are prepared by at least two routes, each of which uses a 2-mercaptobenzimidazole of Formula II. In the preferred route, the 2-mercaptobenzimidazole reacts with a 2-aminobenzyl halide (Formula III in which Y is a halogen, preferably chlorine or bromine). Typical conditions include reaction at room temperature in an organic solvent such as absolute ethanol or isopropyl alcohol. For those compounds which form hydrohalide salts, the corresponding neutral compounds of Formula IV are readily obtained by methods known to those skilled in the art. For example, treating such a salt with base (such as aqueous potassium carbonate), followed by extraction into a non-protic organic solvent (such as dichloromethane or chloroform), gives the free base form of an intermediate of Formula IV.

The 2-aminobenzyl halides of (Formula III in which Y is halogen) are obtained commercially or are prepared from corresponding 2-aminobenzyl alcohols (Formula III in which Y is OH) by synthetic methods well known in the art. For example, reaction of the alcohol with a halogenating reagent, such as thionyl chloride, phosphorus oxychloride, oxalyl chloride, and the like, in an inert organic solvent, such as dichloromethane or chloroform, will give corresponding 2-aminobenzyl chlorides as the hydrochloride salts. A preferred method involves heating the alcohol in

SCHEME A

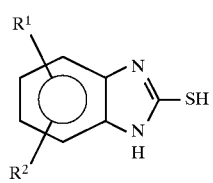

+

-continued
SCHEME A

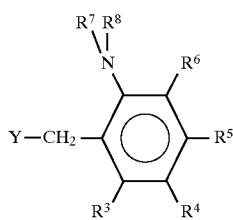

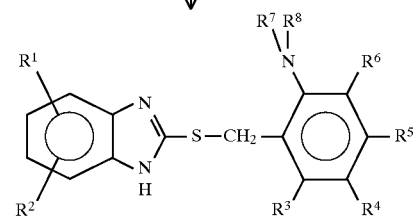

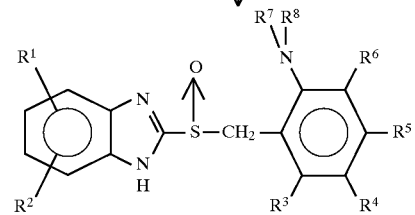

concentrated hydrochloric or hydrobromic acid at temperatures of 80° to 100°. See B. Beilenson and F. M. Hamer, *J. Chem. Soc.*, 98–102 (1942).

Where an appropriate 2-aminobenzyl halide of Formula III is not readily available, intermediates of Formula IV may also be prepared by an acid-catalyzed reaction of the 2-mercaptobenzimidazole of Formula II with 2-aminobenzyl alcohols. Preferred conditions include heating a mixture of compounds of Formulas II and III in glacial acetic acid containing excess (relative to II and III) sulfuric acid. After quenching the reaction by pouring the mixture over ice, the intermediate compounds IV are isolated by methods known in the art, including recrystallization and chromatography. Where an initially required 2-aminobenzyl alcohol is not commercially available, corresponding 2-aminobenzoic acids or 2-aminobenzaldehydes may be reduced using methods known in the art, such as hydrogenation, reaction with lithium aluminum hydride, and the like. Various methods for preparing appropriate aminobenzoic acids are known. See, e.g., Baker et al., *J. Org. Chem.*, 17, 141–148, 149–156 (1952). Corresponding 2-nitrobenzyl alcohols or 2-nitrobenzaldehydes may also be reduced using methods known in the art, such as catalytical hydrogenation, to provide the 2-aminobenzyl alcohols.

The sulfoxide compounds of this invention, Formula I, are prepared by oxidation of the intermediates of Formula IV using methods known to those skilled in the art. Commonly used oxidizing agents include, for example, peracids, such as m-chloroperoxybenzoic acid; peresters; peroxides, such as hydrogen peroxide; sodium metaperiodate; selenium dioxide; manganese dioxide; iodosobenzene; and the like. Preferred conditions for preparing sulfoxides of Formula I include oxidizing intermediates IV with an approximately equimolar quantity of m-chloroperoxybenzoic acid in an organic solvent, such as dichloromethane, at temperatures below 0°. Oxidization may be terminated by adding dimethylsulfide.

Acid addition salts of this invention may be prepared during the course of the reactions (as described above), by ion exchange from those salts using methods known in the art, or by acidification of free bases of the compounds. Base addition salts of this invention by methods known in the art, including those methods disclosed in British Patent No. 2,137,616.

Although some of the 2-mercaptobenzimidazoles of Formula II are commercially available, others may be prepared by synthetic methods known to those skilled in the art. For example, Scheme B illustrates the preparation of 2-mercaptobenzimidazoles from substituted diaminobenzenes of Formula V.

SCHEME B

A preferred cyclization method employs an alkylxanthate salt. Preferred conditions include heating an aqueous mixture of a diaminobenzene of Formula V and potassium ethylxanthate at reflux under an inert atmosphere, such as argon.

The preferred embodiments of this invention include compounds of the following general structure, Formula VI.

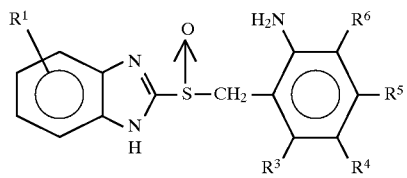

More specifically, the preferred embodiments include compounds of Formula VI wherein $R^1$ is hydrogen or methoxy and wherein $R^3$, $R^4$, $R^5$, and $R^6$, each being the same or different, are hydrogen, alkyl of 1 to 4 carbon atoms, inclusive, or methoxy.

The most preferred embodiments of this invention include compounds of the following general structure, Formula VII.

SCHEME B

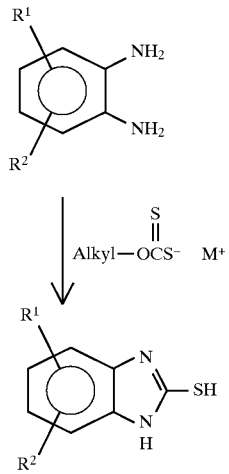

-continued
SCHEME B

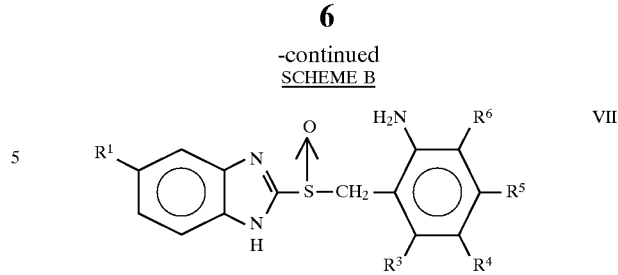

More specifically, the most preferred embodiments include compounds of Formula VII wherein $R^1$ is hydrogen or methoxy and wherein at least one of $R^3$, $R^4$, $R^5$, and $R^6$ is methyl, the others being hydrogen.

The compounds of this invention exhibited gastric antisecretory activity in canines, as indicated by inhibition in vitro of $(H^+ + K^+)$-ATPase obtained from canine gastric mucosa and by inhibition in vivo of gastric acid secretion in dogs. The antisecretory activity of the compounds of this invention illustrated in the Examples was determined by the following methods.

Inhibition of $(H^+ + K^+)$-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000×g for twenty minutes and the pellet discarded. The supernatant was then centrifuged at 150,000×g for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15%–30% sucrose interface, after centrifugation at 250,000×g for sixty minutes, were used as the source of $(H^+ + K^+)$-ATPase. Microsomal preparations were lyophilized, a process that assured potassium ion permiability, and stored at −10° until used.

$(H^+ + K^+)$-ATPase activity for each test compound was determined, in duplicate, by measuring the release of inorganic phosphate, which was assayed according to the method of J. ChandraRajan and L. Klein. Anal. Biochem., 72, 407–412 (1976). The $(H^+ + K^+)$-ATPase assay medium consisted of 20 mM Mes-Tris (pH 6.0), 5 mM magnesium chloride, 25 mM sucrose, and 4 mM Tris-ATP with or without 20 mM potassium chloride in a total volume of 2 ml. Microsomal suspensions (20 to 60 mcl, containing about 25 mcg protein) were added to the assay medium, without Tris-ATP, and then preincubated with a test compound for thirty minutes at 37°. The assay was initiated by adding Tris-ATP and the mixture was incubated another thirty minutes at 37°. A 200-mcl aliquot of the assay mixture was then added to 1.4 ml of a solution consisting of 0.1M sodium acetate (pH 4.0) and 10% sodium dodecylsulfate, followed by the addition of 200 mcl each of 1% ammonium molybdate and 1% ascorbic acid. At least fifteen minutes later, the optical absorbance at 870 nm (which was proportional to inorganic phosphate concentration up to 100 nmoles per tube, as determined by a standard curve) was obtained. Enzyme activity was linear with incubation time.

($H^+ + K^+$)-ATPase activity is represented by the difference between the measured activities in the presence of potassium ion ($K^+$-stimulated) and in the absence of potassium ion (basal). The concentration of a test compound required to inhibit 50% of the ($H^+ + K^+$)-ATPase activity (i.e., the $IC_{50}$) was determined at least in duplicate using linear regression analysis of results obtained for three different compound concentrations ranging from 0.1 mcM to 0.2 mM. If the $IC_{50}$ for a test compound could not be determined for the concentration range tested, percent inhibition of ($H^+ + K^+$)-ATPase was obtained for the compound at 0.1 mM.

Inhibition of Gastric Acid Secretion in Gastric Fistula Beagle Dogs

Adult female beagle dogs weighing 6 to 11 kilograms obtained from Laboratory Research Enterprises (Kalamazoo, Mich.) or from Hazelton Research Animals (Cumberland, Va.) were surgically implanted with a simple Thomas-type gastric cannula. After recovery from surgery, the dogs were trained to stand quietly, fully conscious, in Pavlov-type dog restraining slings and were acclimated to intravenous infusion of histamine dihydrochloride. During the course of these studies, no dog was used more than once a week. All dogs were deprived of food, but not water, for 18 hours prior to each assay. Each dog was initially infused with 0.15M sodium chloride solution at a constant rate of 6.5 mg/hr. The volume of gastric secretions, collected in plastic bottles affixed to the cannula, were measured to the nearest 0.1 ml at 30 minute intervals. One of the following protocols was followed, depending on the route chosen for administration of test compound.

Intravenous dosing: Following a 30-minute basal secretion period, test compounds were administered intravenously. At the end of an additional 30 minute period, the saline infusion was replaced with histamine dihydrochloride in saline administered at a rate 15 mcg per kilogram of body weight per hour. Histamine stimulation was maintained for a maximum of four hours during which time gastric secretions were collected every 30 minutes. The pH and titratable acidity were determined for samples from each collection period.

Intragastric dosing: Following a 30-minute basal secretion period, the collection bottles were removed, dosing plugs were inserted, and test compounds were administered intragastrically. At the end of a 30-minute drug absorption period, the stomachs were emptied, the collection bottles were reattached, and collections were resumed at 30-minute intervals. Simultaneously, the saline infusion was replaced with a continuous intravenous infusion of histamine dihydrochloride in saline administered for four hours at a rate 15 mcg per kilogram of body weight per hour.

Intraduodenal dosing: Dogs were also equipped with duodenal cannulas for intraduodenal (ID) administration of test compounds. Dosing was otherwise performed as described for intragastric dosing.

Data from each protocol were analyzed for three gastric sample variables: volume of gastric juice, acid concentration, and total acid output. Percent inhibition for each four-hour experimental period was determined for each parameter by comparison with 3 to 4 controls in which only food was given. Estimates of $ED_{50}$'s were determined from dose response curves.

Inhibition of Gastric Acid Secretion in Meal-Stimulated Pavlov Pouch Dog

Adult female beagle dogs weighing 6 to 10 kilograms were obtained from Laboratory Research Enterprises (Kalamazoo, Mich.) or from Hazelton Research Animals (Cumberland, Va.). Surgical implantation of a Thomas-type gastric cannula into an innervated Pavlov pouch of each dog was performed by the method reported by L. Burrows et al., *J. Surgical Res.*, 4, 147–150 (1964). After recovery from surgery, the dogs were trained to stand quietly, fully conscious, in Pavlov-type dog restraining slings. All dogs were deprived of food, but not water, for 24 hours prior to each assay. Basal acid secretion was measured by collecting from the cannulas for 30 minutes before dosing with a test compound. Solutions of the test compounds in iso-osmotic phosphate buffer (pH 7.4) were given either intravenously or directly into the Pavlov pouch. After 30 minutes the pouch was drained. The dogs were then fed 320 grams of dog food and gastric acid secretions were collected each half hour for four hours. Controls were determined in the same way except that only food (i.e., no test compound) was administered.

Data were analyzed for three different variables: volume of gastric juice, acid concentration, and total acid output. Percent inhibition for the four-hour experimental period was determined for each parameter by comparison with 3 to 4 controls. Estimates of $ED_{50}$ were determined from dose response curves.

By virtue of their gastric antisecretory activity, the compounds of Formula I are useful in treating ulcers in mammals. A physician or veterinarian of ordinary skill can readily determine whether a subject has ulcers. Regardless of the route of administration selected, the compounds of the present invention are formulated into pharmaceutically acceptable dosage forms by conventional methods known to those skilled in the art. The compounds may be formulated using pharmaceutically acceptable acid addition or base addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating ulcers with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mcg/kg to 500 mg/kg, preferably in the range of about 10 to 100 mg/kg orally or about 1.0 to 20 mg/kg intravenously.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

EXAMPLE 1

2-[(1H-benzimidazol-2-ylthio)methyl]-N,N-dimethylbenzenamine

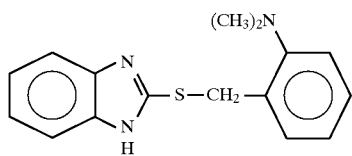

A mixture of 2.20 g (14.6 mmole) of 2-mercaptobenzimidazole and 3.0 g (14.6 mmole) of 2-(chloromethyl)-N,N-dimethylaniline in 120 ml of absolute ethanol were stirred under nitrogen for about two hours. A solid (4.8 g) was collected by filtration, washed with ethanol, and air-dried. The solid was dissolved in water and made basic with potassium carbonate, then extracted into dichloromethane. The organic phase was dried over sodium sulfate, filtered, and concentrated in vacuo to dryness. Recrystallization from acetonitrile gave 2.3 g of a white solid (first crop). Concentration of the acetonitrile liquors gave 0.7 g of a second crop. The two crops were combined and recrystallized from isopropyl alcohol, giving the title compound as an analytically pure solid, m.p. 167°–170°.

Analysis. Calcd. for $C_{16}H_{17}N_3S$: C, 67.81; H, 6.05; N, 14.83; S, 11.31. Found: C, 67.84; H, 6.19; N, 14.73; S, 11.50.

EXAMPLE 2

2-[(1H-benzimidazol-2-ylthio)methyl]benzenamine

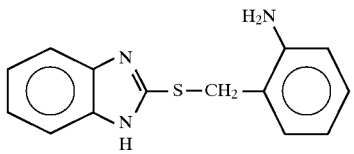

A mixture of 9.0 g (60 mmole) of 2-mercaptobenzimidazole and 4.9 g (40 mmole) of 2-aminobenzyl alcohol were heated at 84° in a mixture of 45 ml of glacial acetic acid and 12.0 g (120 mmole) of sulfuric acid. After two hours an additional 1 g (8 mmole) of 2-aminobenzyl alcohol and 1 g of sulfuric acid were added. After one hour the reaction mixture was cooled and poured into cold (ca. 0°) water containing excess sodium hydroxide. The resultant gummy precipitate was extracted with four portions of dichloromethane. All but the first organic extracts were combined, dried over sodium sulfate, filtered, and concentrated in vacuo. Recrystallization from acetonitrile gave 950 mg of the title compound; column chromatography of the material contained in the liquors on silica gel gave additional title compound, which was recrystallized acetonitrile to give 1.1 g of the title compound as an analytically pure solid, m.p. 146°–148°.

Analysis. Calcd. for $C_{14}H_{13}N_3S$: C, 65.86; H, 5.13; N, 16.46; S, 12.56. Found: C, 65.73; H, 5.20; H, 16.63; S, 12.46.

EXAMPLE 3

2-[(1H-benzimidazol-2-ylsulfinyl)methyl] benzenamine hemihydrate

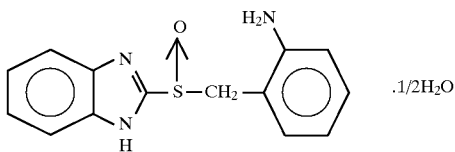

The title product of Example 2 (830 mg, 3.25 mmole) was dissolved in about 200 ml of boiling chloroform and then cooled to about −10°. A solution of 662 mg (ca. 3.25 mmole) of ca. 85% m-chloroperoxybenzoic acid in 10 ml of chloroform was then added with stirring over about ten minutes. After another thirty minutes, the reaction was quenched with 4 drops of dimethylsulfide and a white solid was collected by filtration. The solid was washed sequentially with chloroform and diethyl ether, then air dried, giving 550 mg of the title compound, m.p. 164°–165°.

Analysis. Calcd. for $C_{14}H_{13}N_3OS \cdot \frac{1}{2} H_2O$: C, 59.98; H, 5.03; N, 15.00; S, 11.44. Found: C, 60.11; H, 4.82; N, 14.93; S, 11.44.

EXAMPLE 4

2-[(1H-benzimidazol-2-ylsulfinyl)methyl]-N,N-dimethylbenzenamine

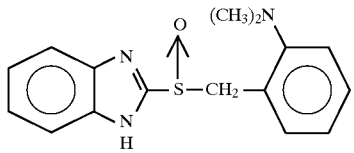

The title compound was prepared by the method of Example 3 using 1.5 g of the title product of Example 1 instead of the title product of Example 2. Recrystallization from diethyl ether gave 786 mg of the title compound, m.p. 107°–109°.

Analysis. Calcd. for $C_{16}H_{17}N_3OS$: C, 64.19; H, 5.72; N, 14.04; S, 10.71. Found: C, 64.44; H, 5.83; N, 14.12; S, 11.06.

EXAMPLE 5

N-[2-[(1H-benzimidazol-2-ylthio)methyl]phenyl]acetamide

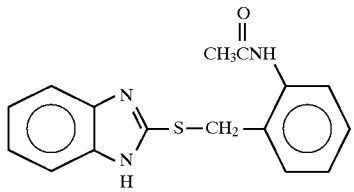

A solution of 10 g (81.3 mmole) of 2-aminobenzyl alcohol and 50 ml (ca. 530 mmole) of acetic anhydride was allowed to stand in 200 ml of pyridine for 20 hours. The solution was concentrated in vacuo and the resultant solid was washed with diethyl ether. The resultant diacetyl intermediate was collected as white needles. A mixture of 7.30 g (35.3 mmole) of the intermediate and 7.30 g (52.9 mmole) of potassium carbonate was stirred for 30 minutes in 300 ml of methanol. After removing insolubles by filtration, the filtrate was concentrated to give the N-acetyl intermediate. The material was suspended in 1 liter of dichloromethane to which was added 10 ml (ca. 137 mmole) of thionyl chloride. After 19 hours the reaction mixture was concentrated to dryness. Chloroform was added to the residue and then removed in vacuo to give crude N-(2-chloromethyl phenyl)acetamide, which was used in the subsequent reaction without further purification. Using the method described in Example 1 with N-(2-chloromethylphenyl)acetamide instead of 2-(chloromethyl)-N,N-dimethylaniline produced 3.9 g of the title compound, m.p. 218°–222°.

Analysis. Calcd. for $C_{16}H_{15}N_3OS$: C, 64.62; H, 5.08; N, 14.13; S, 10.78. Found: C, 64.20; H, 5.20; N, 14.02; S, 11.06.

EXAMPLE 6

N-[2-[(1H-benzimidazol-2-ylsulfinyl)methyl]phenyl]acetamide

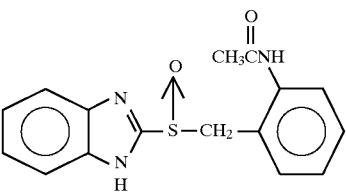

The title compound was prepared by the method of Example 3 using 1.80 g of the title product of Example 5 instead of the title product of Example 2. Trituration with diethyl ether gave 1.52 g of the title compound, m.p. 201°–202.5°.

Analysis. Calcd. for $C_{16}H_{15}N_3O_2S$: C, 61.32; H, 4.82; N, 13.41; S, 10.23. Found: C, 61.00; H, 4.90; N, 13.28; S, 10.50.

EXAMPLE 7

2-[[(4-methyl-1H-benzimidazol-2-yl)thio]methyl]benzenamine

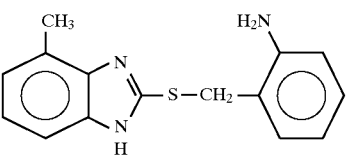

The title compound was prepared by the method of Example 1 using 3.52 g of 2-mercapto-4-methylbenzimidazole instead of 2-mercaptobenzimidazole and 3.52 g of 2-(chloromethyl) aniline hydrochloride instead of 2-(chloromethyl)-N,N-dimethylaniline. Recrystallization from diethyl ether gave 1.23 g of the title compound, m.p. 125°–127°.

Analysis. Calcd. for $C_{15}H_{15}N_3S$: C, 66.89; H, 5.61; N, 15.60; S, 11.90. Found: C, 66.76; H, 5.62; N, 15.41; S, 11.87.

EXAMPLE 8

2-[[(4-methyl-1H-benzimidazol-2-yl)sulfinyl]methyl]benzenamine hemihydrate

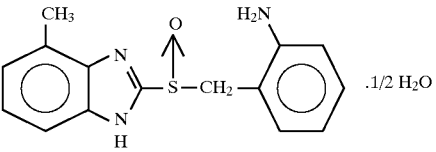

The title compound (740 mg) was prepared by the method of Example 3 using 900 mg of the title product of Example 7 instead of the title product of Example 2.

Analysis. Calcd. for $C_{15}H_{15}N_3OS \cdot \frac{1}{2} H_2O$: C, 61.20; H, 5.48; N, 14.27; S, 10.89. Found: C, 61.21; H, 5.05; N, 13.88; S, 11.12.

EXAMPLE 9

2-[[(5,6-dimethyl-1H-benzimidazol-2-yl)thio]methyl]benzenamine

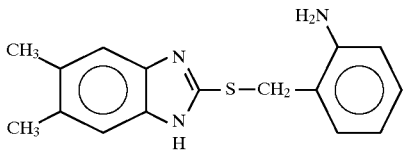

The title compound was prepared by the method of Example 1 using 2.56 g of 5,6-dimethyl-2-mercaptobenzimidazole instead of 2-mercaptobenzimidazole and 2.56 g of 2-(chloromethyl)aniline hydrochloride instead of 2-(chloromethyl)-N,N-dimethylaniline. Instead of using sodium carbonate in an extraction, the crude precipitate was neutralized with triethylamine in methanol. Trituration of the resultant crude title compound with methanol and diethyl ether gave 2.0 g of analytically pure title compound.

Analysis. Calcd. for $C_{15}H_{15}N_3S$: C, 67.81; H, 6.05; N, 14.83; S, 11.31. Found: C, 67.21; H, 6.16; N, 14.50; S, 11.06.

EXAMPLE 10

2-[[(5,6-dimethyl-1H-benzimidazol-2-yl) sulfinyl]methyl]benzenamine ¼ hydrate

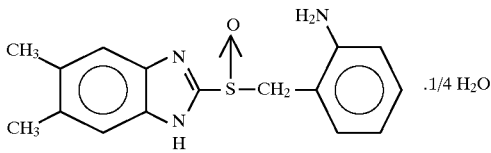

The title compound, m.p. 179°–181°, was prepared by the method of Example 3 using 1.52 g of the title product of Example 9 instead of the title product of Example 2.

Analysis. Calcd. for $C_{16}H_{17}N_3OS \cdot \frac{1}{4} H_2O$: C, 63.24; H, 5.80; N, 13.83; S, 10.55. Found: C, 62.80; H, 5.49; N, 13.53; S, 10.76.

EXAMPLE 11

2-[[(5-methoxy-1H-benzimidazol-2-yl)thio]methyl]benzenamine

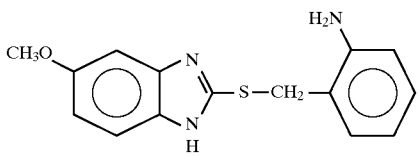

The title compound was prepared by the method of Example 1 using 1.68 g (9.33 mmole) of 2-mercapto-5-methoxybenzimidazole instead of 2-mercaptobenzimidazole and 1.99 g (11.2 mmole) of 2-(chloromethyl)aniline hydrochloride instead of 2-(chloromethyl)-N,N-dimethylaniline in 250 ml of isopropyl alcohol. The basic extraction used 5% sodium hydroxide instead of sodium carbonate. Chromatography on silica gel, followed by crystallization from diethyl ether, gave 520 mg of pure title compound, m.p. 140°–142°.

Analysis. Calcd. for $C_{15}H_{15}N_3OS$: C, 63.14; H, 5.30; N, 14.73; S, 11.23. Found: C, 63.44; H, 5.42; N, 14.43; S, 11.07.

EXAMPLE 12

2-[[(5-methoxy-1H-benzimidazol-2-yl) sulfinyl]methyl]benzenamine

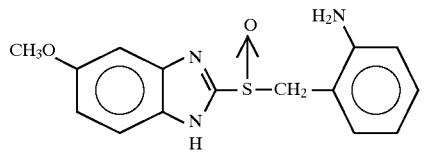

The title compound was prepared by the method of Example 3 using 1.20 g of the title product of Example 11 instead of the title product of Example 2. Trituration with diethyl ether gave 1.04 g of the title compound, m.p. 147°–148°.

Analysis. Calcd. for $C_{15}H_{15}N_3O_2S$: C, 59.78; H, 5.02; N, 13.94; S, 10.64. Found: C, 59.30; H, 4.95; N, 13.55; S, 10.73.

EXAMPLE 13 methyl 2-[[(2-aminophenyl)methyl]thio]-5-methoxy-1H-benzimidazole-6-carboxylate, dihydrochloride

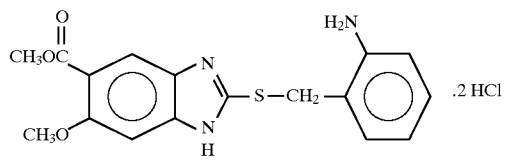

To a mixture of 29.0 g (0.16 mole) of methyl 4-amino-2-methoxybenzoate, 0.5 g of 4-dimethylaminopyridine, and 16.0 gm (0.16 mole) of triethylamine in 500 ml of dichloromethane was added in batches 22 ml (ca. 0.23 mole) of acetic acid. After two hours the reaction mixture was neutralized with sodium bicarbonate (in solution and as a solid). The organic phase was washed successively with aqueous sodium bicarbonate. The organic phase was washed successively with aqueous sodium bicarbonate and brine, dried over magnesium sulfate, filtered, and concentrated in vacuo. Recrystallization from toluene gave 30 g of methyl 4-acetamido-2-methoxybenzoate. To 100 ml of fuming nitric acid, stirred at –40°, was slowly added 22.3 g (0.10 mole) of the acetylated intermediate. After about twenty minutes the mixture was allowed to warm to and to stir at 0° for another twenty minutes. The mixture was poured onto one liter of ice and the resultant precipitate was collected. Recrystallization from toluene/ethanol gave 14.2 g of the nitrated and deacetylated compound, methyl 4-amino-2-methoxy-5-nitrobenzoate. (Under similar conditions in which the acetyl group is not removed, saponification with methanolic sodium hydroxide gives the same product.) Hydrogenation of the nitro intermediate in tetrahydrofuran using Raney nickel as catalyst gave methyl 4,5-diamino-2-methoxybenzoate. A mixture of 4.83 g (24.6 mmole) of the diamine and 7.08 g (49.2 mmole) of potassium ethylxanthate was heated at reflux under argon in 40 ml of water. The resultant product mixture was chromatographed on silica gel to give 1.5 g of methyl 2-mercapto-5-methoxy-1H-benzimidazole-6-carboxylate. (Analysis. Calcd. for $C_{10}H_{10}N_2O_3S$: C, 50.41; H, 4.23; N, 11.76; S, 13.46. Found: C, 50.30; H, 4.19; N, 11.71; S, 13.12.) The title compound was then prepared by the method of Example 1 using 1.19 g (5.0 mmole) of methyl 2-mercapto-5-methoxy-1H-benzimidazole-6-carboxylate instead of 2-mercaptobenzimidazole and 0.97 g (5.5 mmole) of

EXAMPLE 14 methyl 2-[[(2-aminophenyl)methyl]sulfinyl]-5-methoxy-1H-benzimidazole-6-carboxylate

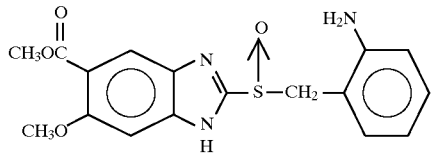

The title compound is prepared by the method of Example 3 using the title product of Example 11 instead of the title product of Example 2.

EXAMPLE 15

2-[(1H-benzimidazol-2-ylthio)methyl]-4-chlorobenzenamine

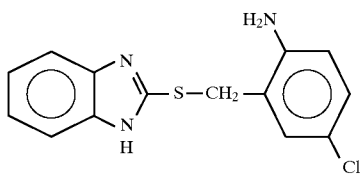

The title compound was prepared by the method of Example 1 using 6.0 g of 2-(bromomethyl)-4-chloroaniline hydrobromide instead of 2-(chloromethyl)-N,N-dimethylaniline and isopropyl alcohol instead of ethanol. Concentration to dryness, chromatography on silica gel, and crystallization from methanol to which was added water, gave 343 mg of the title compound, m.p. 114°–118°.

Analysis. Calcd. for $C_{14}H_{12}N_3ClS$: C, 58.02; H, 4.17; N, 14.50; Cl, 12.23; S, 11.06. Found: C, 58.16; H, 4.24; N, 14.44; Cl, 12.35; S, 11.35.

EXAMPLE 16

2-[(1H-benzimidazol-2-ylsulfinyl)methyl]-4-chlorobenzenamine

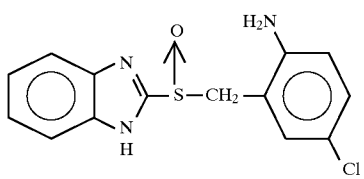

The title compound was prepared by the method of Example 3 using 1.36 g of the title product of Example 15 instead of the title product of Example 2 and dichloromethane instead of chloroform. After the initial trituration, purification was effected using chromatography on silica gel. Trituration with methanol/dichloromethane gave 316 mg of the title compound, m.p. 210°–211°.

Analysis. Calcd. for $C_{14}H_{13}N_3OClS$: C, 54.99; H, 3.96; N, 13.74; Cl, 11.59; S, 10.48. Found: C, 54.87; H, 3.91; N, 13.55; Cl, 12.26; S, 10.61.

2-(chloromethyl)aniline hydrochloride instead of 2-(chloromethyl)-N,N-dimethylaniline.

Analysis. Calcd. for $C_{17}H_{17}N_3O_3S \cdot 2HCl$: C, 49.05; H, 4.60; N, 10.09; S, 7.70; Cl, 17.03. Found: C, 49.37; H, 4.77; N, 9.72; S, 7.43; Cl, 16.77.

EXAMPLE 17

2-[(1H-benzimidazol-2-ylthio)methyl]-5-chlorobenzenamine

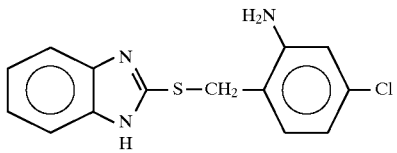

The title compound was prepared by the method of Example 1 using 5.40 g of 2-(bromomethyl)-5-chloroaniline hydrobromide instead of 2-(chloromethyl)-N,N-dimethylaniline in 100 ml of isopropyl alcohol. Chromatography on silica gel and recrystallization from acetonitrile gave 160 mg of the title compound, m.p. 158°–160.5°.

Analysis. Calcd. for $C_{14}H_{12}N_3ClS$: C, 58.03; H, 4.17; N, 12.23; S, 11.06. Found: C, 57.95; H, 4.22; N, 14.41; Cl, 12.54; S, 10.96.

EXAMPLE 18

2-[(1H-benzimidazol-2-ylsulfinyl)methyl]-5-chlorobenzenamine

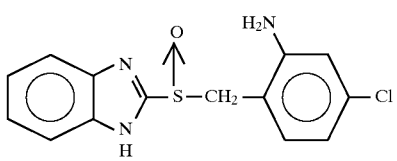

The title compound was prepared by the method of Example 3 using 1.13 g of the title product of Example 17 instead of the title product of Example 2. Trituration with chloroform gave 1.04 g of the title compound, m.p. 173.5°–175.5°.

Analysis. Calcd. for $C_{14}H_{12}N_3ClOS$: C, 54.99; H, 3.96; N, 13.74; Cl, 11.59; S, 10.48. Found: C, 54.37; H, 3.99; N, 13.43; Cl, 11.52; S, 10.21.

EXAMPLE 19

2-[(1H-benzimidazol-2-ylthio)methyl]-4-methoxybenzenamine dihydrochloride

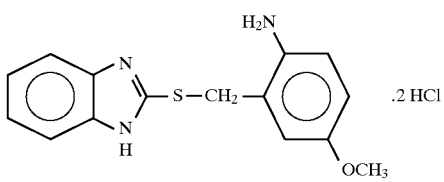

The title compound was prepared by the method of Example 1 using 2.85 g of 2-(chloromethyl)-4-methoxyaniline hydrochloride instead of 2-(chloromethyl)-N,N-dimethylaniline. The precipitate was not neutralized with base but was instead washed sequentially with ethanol and diethyl ether, giving 2.56 g of the title compound as the dihydrochloride, m.p. 206°–208°.

Analysis. Calcd. for $C_{15}H_{15}N_3OS \cdot 2HCl$: C, 50.29; H, 4.78; N, 11.73; S, 8.95; Cl, 19.79. Found: C, 49.95; H, 4.57; N, 11.55; S, 9.07; Cl, 19.09.

EXAMPLE 20

2-[(1H-benzimidazol-2-ylsulfinyl)methyl]-4-methoxybenzenamine

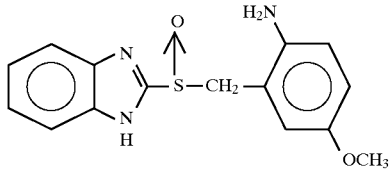

The title compound was prepared by the method of Example 3 using 2.20 g of the free base of the title product of Example 19 instead of the title product of Example 2. Trituration with diethyl ether gave 900 mg of the title compound, m.p. 152°–153°.

Analysis. Calcd. for $C_{15}H_{15}N_3O_2S$: C, 59.78; H, 5.02; N, 13.94; S, 10.64. Found: C, 59.01; H, 4.97; N, 13.65; S, 10.65.

EXAMPLE 21

2-[(1H-benzimidazol-2-ylthio)methyl]-6-methoxybenzenamine hemihydrate

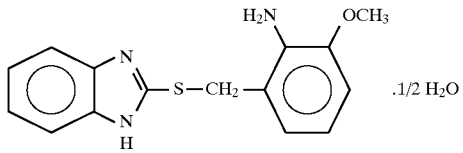

The title compound was prepared by the method of Example 1 using 4.16 g of 2-(chloromethyl)-6-methoxyaniline hydrochloride instead of 2-(chloromethyl)-N,N-dimethylaniline. Trituration with diethyl ether gave 2.40 g of the title compound.

Analysis. Calcd. for $C_{15}H_{15}N_3OS.½ H_2O$: C, 61.20; H, 5.48; N, 14.27; S, 10.89. Found: C, 61.79; H, 5.10; N, 14.72; S, 11.10.

EXAMPLE 22

2-[(1H-benzimidazol-2-ylsulfinyl)methyl]-6-methoxybenzenamine hemihydrate

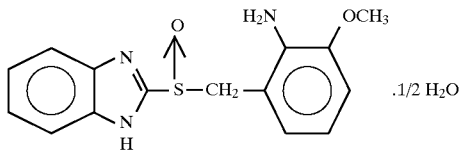

The title compound was prepared by the method of Example 3 using 1.50 g of the title product of Example 21 instead of the title product of Example 2. The reaction mixture was concentrated in vacuo and triturated with diethyl ether. After filtration, the filtrate deposited 202 mg of the title compound, m.p. 141°–143°.

Analysis. Calcd. for $C_{15}H_{15}N_3O_2S.½ H_2O$: C, 58.05; H, 5.20; N, 13.54; S, 10.33. Found: C, 57.65; H, 5.17; N, 13.19; S, 10.50.

EXAMPLE 23

2-[(1H-benzimidazol-2-ylthio)methyl]-3-methylbenzenamine

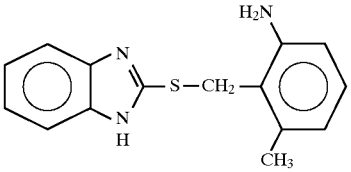

The title compound was prepared by the method of Example 1 using 3.55 g of 2-(chloromethyl)-3-methylaniline hydrochloride instead of 2-(chloromethyl)-N,N-dimethylaniline. Trituration with diethyl ether gave 2.31 g of the title compound.

Analysis. Calcd. for $C_{15}H_{15}N_3S$: C, 66.89; H, 5.61; N, 15.60; S, 11.90. Found: C, 66.61; H, 5.53; N, 15.52; S, 11.80.

EXAMPLE 24

2-[(1H-benzimidazol-2-ylsulfinyl)methyl]-3-methylbenzenamine ¼ hydrate

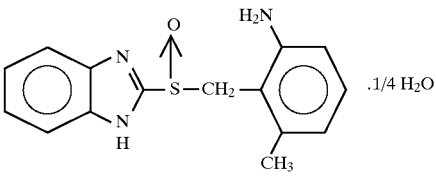

The title compound was prepared by the method of Example 3 using 1.07 g of the title product of Example 23 instead of the title product of Example 2. Trituration with dichloromethane gave 327 mg of the title compound, m.p. 152°–153°.

Analysis. Calcd. for $C_{15}H_{15}N_3OS.¼ H_2O$: C, 62.21; H, 5.31; N, 14.51; S, 11.07. Found: C, 62.28; H, 5.05; N, 14.46; S, 11.22.

EXAMPLE 25

2-[(1H-benzimidazol-2-ylthio)methyl]-4-methylbenzenamine

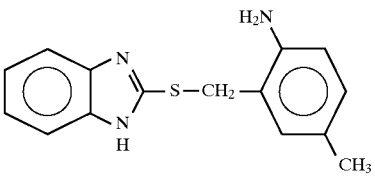

The title compound was prepared by the method of Example 1 using 2-(chloromethyl )-4-methylaniline hydrochloride instead of 2-(chloromethyl)-N,N-dimethylaniline. Chromatography on silica gel gave 650 mg of the title compound.

Analysis. Calcd. for $C_{15}H_{15}N_3S$: C, 66.89; H, 5.61; N, 15.60; S, 11.90. Found: C, 66.70; H, 5.65; N, 15.50; S, 11.85.

EXAMPLE 26

2-[(1H-benzimidazol-2-ylsulfinyl)methyl]-4-methylbenzenamine

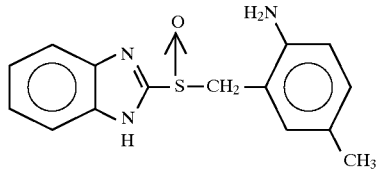

The title compound was prepared by the method of Example 3 using 2.68 g of the title product of Example 25 instead of the title product of Example 2 and using 1,2-dichloroethane as solvent instead of chloroform. Trituration with diethyl ether gave 3.0 g of the title compound.

Analysis. Calcd. for $C_{15}H_{15}N_3OS$: C, 63.14; H, 5.30; N, 14.73; S, 11.23. Found: C, 61.44; H, 4.98; N, 14.35; S, 11.10.

EXAMPLE 27

2-[(1H-benzimidazol-2-ylthio)methyl]-6-methylbenzenamine

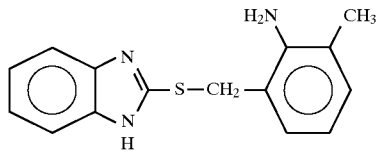

The title compound was prepared by the method of Example 1 using 5.00 g of 2-(chloromethyl)-6-methylaniline hydrochloride instead of 2-(chloromethyl)-N,N-dimethylaniline. Trituration with hexane gave 3.33 g of the title compound, m.p. 130°–134°.

Analysis. Calcd. for $C_{15}H_{15}N_3S$: C, 66.89; H, 5.61; N, 15.60; S, 11.90. Found: C, 66.85; H, 5.61; N, 15.20; S, 11.50.

EXAMPLE 28

2-[(1H-benzimidazol-2-ylsulfinyl)methyl]-6-methylbenzenamine

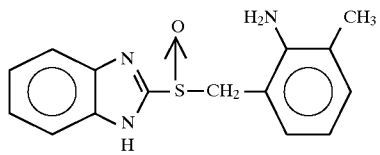

The title compound was prepared by the method of Example 3 using 1.68 g of the title product of Example 27 instead of the title product of Example 2. Trituration with acetonitrile gave 948 mg of the title compound, m.p. 156°–157°.

Analysis. Calcd. for $C_{15}H_{15}N_3OS$: C, 63.14; H, 5.30; N, 14.73; S, 11.23. Found: C, 62.91; H, 5.18; N, 14.33; S, 11.08.

EXAMPLE 29

2-[(1H-benzimidazol-2-ylthio)methyl]-4,6-dimethylbenzenamine

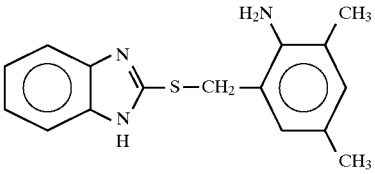

The title compound was prepared by the method of Example 1 using 1.68 g of 2-(chloromethyl)-4,6-dimethylaniline hydrochloride instead of 2-(chloromethyl)-N,N-dimethylaniline. Crystallization from diethyl ether gave 788 mg of the title compound, m.p. 139°–141°.

Analysis. Calcd. for $C_{16}H_{17}N_3S$: C, 67.81; H, 6.05; N, 14.83; S, 11.31. Found: C, 67.30; H, 5.93; N, 14.66; S, 11.29.

EXAMPLE 30

2-[(1H-benzimidazol-2-ylsulfinyl)methyl]-4,6-dimethylbenzenamine hemihydrate

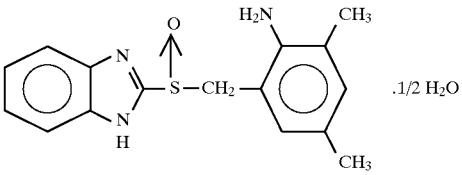

The title compound was prepared by the method of Example 3 using 950 mg of the title product of Example 29 instead of the title product of Example 2. Trituration with diethyl ether gave 434 mg of the title compound.

Analysis. Calcd. for $C_{16}H_{17}N_3OS \cdot \frac{1}{2} H_2O$: C, 62.23; H, 5.88; N, 13.63; S, 10.40. Found: C, 62.39; H, 5.72; N, 13.50; S, 10.65.

EXAMPLE 31

2-[(1H-benzimidazol-2-ylthio)methyl]-N-methylbenzenamine

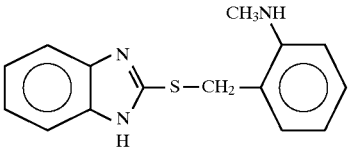

The title compound was prepared by the method of Example 1 using 28.8 g of 2-(chloromethyl)-N-methylaniline hydrochloride instead of 2-(chloromethyl)-N,N-dimethylaniline. Trituration with diethyl ether gave 22.5 g of the title compound, m.p. 109°–112°.

Analysis. Calcd. for $C_{15}H_{15}N_3S$: C, 66.89; H, 5.61; N, 15.60; S, 11.90. Found: C, 66.76; H, 5.72; N, 15.47; S, 11.98.

EXAMPLE 32

2-[(1H-benzimidazol-2-ylsulfinyl)methyl]-N-methylbenzenamine monohydrate

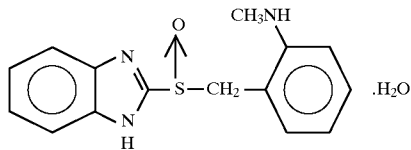

The title compound was prepared by the method of Example 3 using 10.0 g of the title product of Example 31 instead of the title product of Example 2. Trituration with diethyl ether, filtration, and concentration of the filtrate gave 4.33 g of the title compound, m.p. 117°–120°.

Analysis. Calcd. for $C_{15}H_{15}N_3OS \cdot H_2O$: C, 59.39; H, 5.65; N, 13.85; S, 10.57. Found: C, 59.10; H, 5.57; N, 13.92; S, 10.47.

EXAMPLE 33

2-[[(5-methoxy-1H-benzimidazol-2-yl)thio]methyl]-4-methylbenzenamine

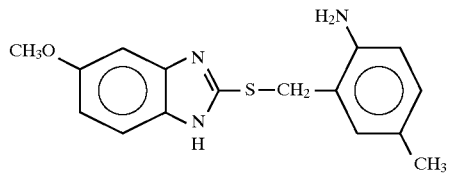

The title compound (1.95 g) was prepared by the method of Example 1 using 2.81 g of 2-mercapto-5-methoxybenzimidazole instead of 2-mercaptobenzimidazole and 3.00 g of 2-(chloromethyl)-4-methylaniline hydrochloride instead of 2-(chloromethyl)-N,N-dimethylaniline.

Analysis. Calcd. for $C_{16}H_{17}N_3OS$: C, 64.19; H, 5.72; N, 14.04; S, 10.71. Found: C, 63.71; H, 5.80; N, 13.86; S, 10.60.

EXAMPLE 34

2-[[(5-methoxy-1H-benzimidazol-2-yl)sulfinyl]methyl]-4-methylbenzenamine

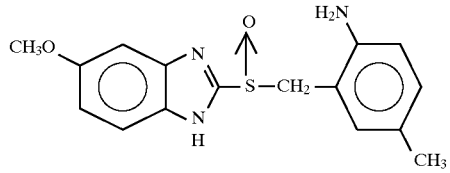

The title compound was prepared by the method of Example 3 using 1.50 g of the title product of Example 33 instead of the title product of Example 2. Concentration to dryness and trituration with diethyl ether gave 1.10 g of the title compound, m.p. 148°–149°.

Anaylsis. Calcd. for $C_{16}H_{17}N_3O_2S$: C, 60.93; H, 5.43; N, 13.32; S, 10.17. Found: C, 60.67; H, 5.38; N, 13.20; S, 9.95.

EXAMPLE 35

2-[[(5-methoxy-1H-benzimidazol-2-yl)thio]methyl]-6-methylbenzenamine

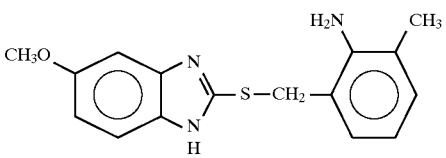

The title compound was prepared by the method of Example 1 using 3.75 g of 2-mercapto-5-methoxybenzimidazole instead of 2-mercaptobenzimidazole and 4.00 g of 2-(chloromethyl)-6-methylaniline hydrochloride instead of 2-(chloromethyl)-N,N-dimethylaniline. Trituration with hexane gave 3.02 g of the title compound, m.p. 132°–134°.

Analysis. Calcd. for $C_{16}H_{17}N_3OS$: C, 64.19; H, 5.72; N, 14.04; S, 10.71. Found: C, 64.21; H, 5.77; N, 14.00; S, 10.38.

EXAMPLE 36

2-[[(5-methoxy-1H-benzimidazol-2-yl)sulfinyl]methyl]-6-methylbenzenamine

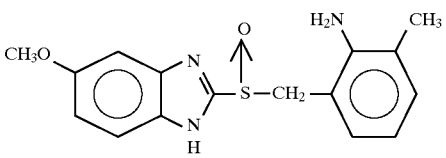

The title compound was prepared by the method of Example 3 using 2.00 g of the title product of Example 35 instead of the title product of Example 2. Trituration with diethyl ether gave 1.58 g of the title compound, m.p. 142°–144°.

Analysis. Calcd. for $C_{16}H_{17}N_3O_2S$: C, 60.93; H, 5.43; N, 13.32; S, 10.17. Found: C, 60.60; H, 5.42; N, 12.83; S, 9.86.

EXAMPLE 37

2-[(1H-benzimidazol-2-ylsulfinyl)methyl]-4-ethylbenzenamine

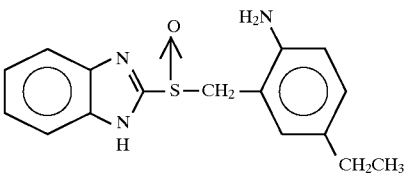

The title compound, m.p. 155°–156°, was prepared by the methods of Examples 1 and 3 using 2-(chloromethyl)-4-ethylaniline hydrochloride instead of 2-(chloromethyl)-N,N-dimethylaniline.

Analysis. Calcd. for $C_{16}H_{17}N_3OS$: C, 64.19; H, 5.72; N, 14.04; S, 10.71. Found: C, 63.86; H, 5.67; N, 14.01; S, 10.68.

EXAMPLE 38

2-[(1H-benzimidazol-2-ylsulfinyl)methyl]-6-ethylbenzenamine

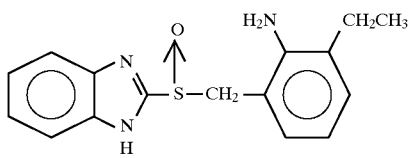

The title compound was prepared by the methods of Examples 1 and 3 using 2-(chloromethyl)-6-ethylaniline hydrochloride instead of 2-(chloromethyl)-N,N-dimethylaniline.

Analysis. Calcd. for $C_{16}H_{17}N_3OS$: C, 64.19; H, 5.73; N, 14.04; S, 10.71. Found: C, 63.88; H, 5.55; N, 13.87, S, 10.57.

EXAMPLE 39

2-[(1H-benzimidazol-2-ylsulfinyl)methyl]-5-methoxy-4,6-dimethylbenzenamine

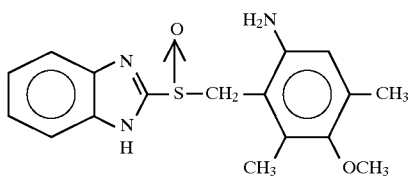

A mixture of 10 g (66.2 mmole) of 4-methoxy-3,5-dimethylaniline and 10 g (67.6 mmole) of phthalic anhydride was heated at 170° for 30 minutes, then allowed to cool overnight to room temperature. Recrystallization from aqueous ethanol gave 16.4 g (58.4 mmole) of the phthalimide derivative. Paraformaldehyde (3 g, 100 mmole) was dissolved in 100 ml of concentrated sulfuric acid and the mixture was cooled to 0°. Hydrogen chloride gas was introduced over a five-minute period, after which the phthalimide derivative was added in small batches. After addition hydrogen chloride gas was introduced for five minutes, the mixture was stirred at 0° for 45 minutes. The mixture was poured over ice, filtered, and washed with water, giving 5.34 g of the phthalimide derivative (m.p. 267°–271°) of 2-hydroxymethyl-4-methoxy-3,5-dimethylaniline. Using the general method of Example 2 with this phthalimide derivative instead of 2-aminobenzyl alcohol and concentrated hydrochloric acid instead of sulfuric acid produced the phthalimide derivative of 2-[(1H-benzimidazol-2-ylthio) methyl]-5-methoxy-4,6-dimethylbenzenamine. Trituration with diethyl ether gave 3.4 g of the analytically pure compound, m.p. 240°–244°. [Analysis. Calcd. for $C_{25}H_{21}N_3O_3S$: C, 67.70; H, 4.77; N, 9.47; S, 7.23. Found: C, 67.57; H, 4.84; N, 9.53; S, 7.31.] Using the method of Example 3 with 3.0 g (6.8 mmole) of this phthalimide derivative instead of the title product of Example 3 produced the corresponding sulfoxide. Trituration with diethyl ether gave 2.81 g of the analytically pure sulfoxide as the ¼ hydrate, m.p. 198.5°–201°. [Analysis. Calcd. for $C_{25}H_{21}N_3O_4S \cdot ¼ H_2O$: C, 64.71; H, 4.67; N, 9.06; S, 6.91. Found: C, 64.82; H, 4.63; N, 9.07; S, 6.96.] The sulfoxide (1.0 g, 2.2 mmole) was dissolved in 50 ml of methanol by warming to 50°–60° and then allowed to cool to room temperature. Hydrazine hydrate (1 ml, ca. 20 mmole) was added and the mixture was stirred for about 5 hours. The resultant suspension was concentrated in vacuo, suspended in water, and treated with about 50 drops of aqueous ammonium hydroxide. The precipitate was collected and washed with dilute ammonium hydroxide to give 0.47 g of the title compound, m.p. 150°–155°.

Analysis. Calcd. for $C_{17}H_{19}N_3O_2S$: C, 61.98; H, 5.81; N, 12.76; S, 9.73. Found: C, 61.66; H, 5.85; N, 12.61; S, 9.34.

EXAMPLE 40

Table of Pharmacological Test Results.

| Compound [Product of Example No.] | $(H^+ + K^+)$-ATPase $IC_{50}$ (mcM) | Gastric-Fistula Beagle % Inhibition (3 mg/kg dose) | Pavlov-Pouch Dog % Inhibition (at dose (mg/kg)) |
|---|---|---|---|
| 3 | 4.3 | 58 | 87 (10 mg/kg) |
| 4 | 0.7 | 14 | 8 (3 mg/kg) |
| 6 | >100 | 26 | |
| 8 | 7.4 | 60 | |
| 10 | 13.5 | 44 | |
| 12 | 11.0 | 89 | 54 (10 mg/kg) |
| 16 | 130.0 | 24 | |
| 18 | 24.0 | 11 | |
| 20 | 1.6 | 37 | 22 (3 mg/kg) |
| 22 | 9.3 | 70 | |
| 24 | 0.66 | 73 | |
| 26 | 2.1 | 67 | |
| 28 | 3.2 | 44 | 43 (3 mg/kg) |
| 30 | 0.85 | | |
| 32 | 0.64 | 21 | |
| 34 | 4.2 | 91 | |
| 36 | 5.4 | 96 | |
| 37 | 2.0 | | |
| 38 | 3.9 | | |

What is claimed is:

1. A compound of the formula:

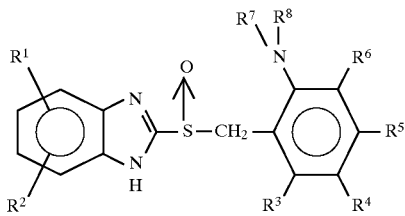

wherein $R^1$ is:

a) hydrogen;

b) alkyl of 1 to 4 carbon atoms, inclusive;

c) alkoxy of 1 to 4 carbon atoms, inclusive; or d) fluorinated alkyl of 1 to 4 carbon atoms, inclusive;

wherein $R^2$ is:

a) hydrogen;

b) alkyl of 1 to 4 carbon atoms, inclusive;

c) fluorinated alkyl of 1 to 4 carbon atoms, inclusive; or d) alkoxycarbonyl of 2 to 6 carbon atoms, inclusive;

wherein $R^3$, $R^4$, $R^5$, and $R^6$, each being the same or different, are:

a) hydrogen;

b) alkyl of 1 to 4 carbon atoms, inclusive;

c) alkoxy of 1 to 4 carbon atoms, inclusive;

d) halogen; or e) fluorinated alkyl of 1 to 4 carbon atoms, inclusive;

wherein $R^7$ is:

a) hydrogen;

b) alkyl of 1 to 4 carbon atoms, inclusive; or
c) alkanoyl of 2 to 6 carbon atoms, inclusive;
wherein R⁸ is:
  a) hydrogen; or
  b) alkyl of 1 to 4 carbon atoms, inclusive; or a pharmaceutically acceptable acid addition salt thereof; or a pharmaceutically acceptable base addition salt thereof.

2. A compound according to claim 1 having the formula:

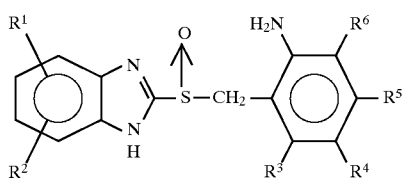

wherein R¹ is:
  a) hydrogen;
  b) alkyl of 1 to 4 carbon atoms, inclusive;
  c) alkoxy of 1 to 4 carbon atoms, inclusive; or
  d) fluorinated alkyl of 1 to 4 carbon atoms, inclusive;
wherein R² is:
  a) hydrogen;
  b) alkyl of 1 to 4 carbon atoms, inclusive;
  c) fluorinated alkyl of 1 to 4 carbon atoms, inclusive; or
  d) alkoxycarbonyl of 2 to 6 carbon atoms, inclusive;
wherein R³, R⁴, R⁵, and R⁶, each being the same or different, are:
  a) hydrogen;
  b) alkyl of 1 to 4 carbon atoms, inclusive;
  c) alkoxy of 1 to 4 carbon atoms, inclusive;
  d) halogen; or
  e) fluorinated alkyl of 1 to 4 carbon atoms, inclusive; or a pharmaceutically acceptable acid addition salt thereof; or a pharmaceutically acceptable base addition salt thereof.

3. A compound according to claim 2 having the formula:

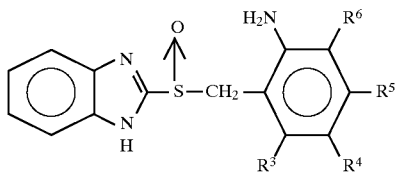

wherein R³, R⁴, R⁵, and R⁶, each being the same or different, are:
  a) hydrogen;
  b) alkyl of 1 to 4 carbon atoms, inclusive;
  c) alkoxy of 1 to 4 carbon atoms, inclusive;
  d) halogen; or
  e) fluorinated alkyl of 1 to 4 carbon atoms, inclusive; or a pharmaceutically acceptable acid addition salt thereof; or a pharmaceutically acceptable base addition salt thereof.

4. A compound according to claim 3, which is 2-[(1H-benzimidazol-2-ylsulfinyl)methyl]benzenamine.

5. A compound according to claim 3, which is 2-[(1H-benzimidazol-2-ylsulfinyl)methyl]-4-chlorobenzenamine.

6. A compound according to claim 3, which is 2-[(1H-benzimidazol-2-ylsulfinyl)methyl]-5-chlorobenzenamine.

7. A compound according to claim 3, which is 2-[(1H-benzimidazol-2-ylsulfinyl)methyl]-4-methoxybenzenamine.

8. A compound according to claim 3, which is 2-[(1H-benzimidazol-2-ylsulfinyl)methyl]-6-methoxybenzenamine.

9. A compound according to claim 3, which is 2-[(1H-benzimidazol-2-ylsulfinyl)methyl]-3-methylbenzenamine.

10. A compound according to claim 3, which is 2-[(1H-benzimidazol-2-ylsulfinyl)methyl]-4-methylbenzenamine.

11. A compound according to claim 3, which is 2-[(1H-benzimidazol-2-ylsulfinyl)methyl]-6-methylbenzenamine.

12. A compound according to claim 3, which is 2-[(1H-benzimidazol-2-ylsulfinyl)methyl]-4-ethylbenzenamine.

13. A compound according to claim 3, which is 2-[(1H-benzimidazol-2-ylsulfinyl)methyl]-6-ethylbenzenamine.

14. A compound according to claim 3, which is 2-[(1H-benzimidazol-2-ylsulfinyl)methyl]-4,6-dimethylbenzenamine.

15. A compound according to claim 3, which is 2-[(1H-benzimidazol-2-ylsulfinyl)methyl]-5-methoxy-4,6-dimethylbenzenamine.

16. A compound according to claim 2 having the formula:

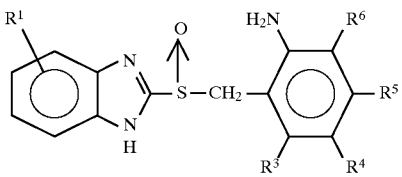

wherein R¹ is:
  a) alkyl of 1 to 4 carbon atoms, inclusive;
  b) alkoxy of 1 to 4 carbon atoms, inclusive; or
  c) fluorinated alkyl of 1 to 4 carbon atoms, inclusive;
wherein R³, R⁴, R⁵, and R⁶, each being the same or different, are:
  a) hydrogen;
  b) alkyl of 1 to 4 carbon atoms, inclusive;
  c) alkoxy of 1 to 4 carbon atoms, inclusive;
  d) halogen; or
  e) fluorinated alkyl of 1 to 4 carbon atoms, inclusive; or a pharmaceutically acceptable acid addition salt thereof; or a pharmaceutically acceptable base addition salt thereof.

17. A compound according to claim 16, which is 2-[[(4-methyl-1H-benzimidazol-2-yl)sulfinyl]methyl]benzenamine.

18. A compound according to claim 16, which is 2-[[(5-methoxy-1H-benzimidazol-2-yl)sulfinyl]methyl]benzenamine.

19. A compound according to claim 16, which is 2-[[(5-methoxy-1H-benzimidazol-2-yl)sulfinyl]methyl]-4-methylbenzenamine.

20. A compound according to claim 16, which is 2-[[(5-methoxy-1H-benzimidazol-2-yl)sulfinyl]methyl]-6-methylbenzenamine.

21. A compound according to claim 2 having the formula:

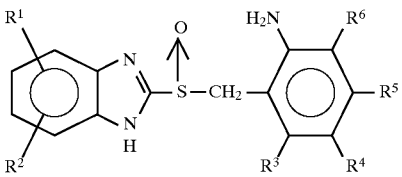

wherein R¹ is:
  a) alkyl of 1 to 4 carbon atoms, inclusive;

b) alkoxy of 1 to 4 carbon atoms, inclusive; or c) fluorinated alkyl of 1 to 4 carbon atoms, inclusive;
wherein $R^2$ is:

a) alkyl of 1 to 4 carbon atoms, inclusive;

b) fluorinated alkyl of 1 to 4 carbon atoms, inclusive; or c) alkoxycarbonyl of 2 to 6 carbon atoms, inclusive;
wherein $R^3$, $R^4$, $R^5$, and $R^6$, each being the same or different, are:

a) hydrogen;

b) alkyl of 1 to 4 carbon atoms, inclusive;

c) alkoxy of 1 to 4 carbon atoms, inclusive;

d) halogen; or e) fluorinated alkyl of 1 to 4 carbon atoms, inclusive; or a pharmaceutically acceptable acid addition salt thereof; or a pharmaceutically acceptable base addition salt thereof.

22. A compound according to claim 21, which is 2-[[(5,6-dimethyl-1H-benzimidazol-2-yl)sulfinyl]methyl] benzenamine.

23. A compound according to claim 21, which is methyl 2-[[(2-aminophenyl)methyl]sulfinyl]-5-methoxy-1H-benzimidazole-6-carboxylate.

24. A compound according to claim 1 having the formula:

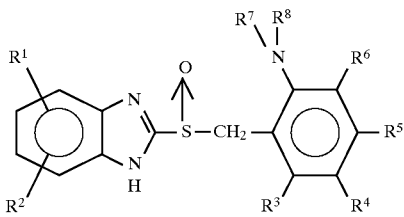

wherein $R^1$ is:

a) hydrogen;

b) alkyl of 1 to 4 carbon atoms, inclusive;

c) alkoxy of 1 to 4 carbon atoms, inclusive; or d) fluorinated alkyl of 1 to 4 carbon atoms, inclusive;
wherein $R^2$ is:

a) hydrogen;

b) alkyl of 1 to 4 carbon atoms, inclusive;

c) fluorinated alkyl of 1 to 4 carbon atoms, inclusive; or d) alkoxycarbonyl of 2 to 6 carbon atoms, inclusive;
wherein $R^3$, $R^4$, $R^5$, and $R^6$, each being the same or different, are:

a) hydrogen;

b) alkyl of 1 to 4 carbon atoms, inclusive;

c) alkoxy of 1 to 4 carbon atoms, inclusive;

d) halogen; or e) fluorinated alkyl of 1 to 4 carbon atoms, inclusive;
wherein $R^7$ is:

a) hydrogen; or b) alkyl of 1 to 4 carbon atoms, inclusive;
wherein $R^8$ is alkyl of 1 to 4 carbon atoms, inclusive; or a pharmaceutically acceptable acid addition salt thereof; or a pharmaceutically acceptable base addition salt thereof.

25. A compound according to claim 24, which is 2-[(1H-benzimidazol-2-ylsulfinyl)methyl]-N-methylbenzenamine.

26. A compound according to claim 24, which is 2-[(1H-benzimidazol-2-ylsulfinyl)methyl]-N,N-dimethylbenzenamine.

27. A compound according to claim 1 having the formula:

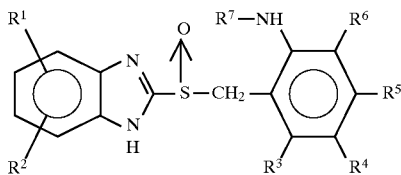

wherein $R^1$ is:

a) hydrogen;

b) alkyl of 1 to 4 carbon atoms, inclusive;

c) alkoxy of 1 to 4 carbon atoms, inclusive; or d) fluorinated alkyl of 1 to 4 carbon atoms, inclusive;
wherein $R^2$ is:

a) hydrogen;

b) alkyl of 1 to 4 carbon atoms, inclusive;

c) fluorinated alkyl of 1 to 4 carbon atoms, inclusive; or d) alkoxycarbonyl of 2 to 6 carbon atoms, inclusive;
wherein $R^3$, $R^4$, $R^5$, and $R^6$, each being the same or different, are:

a) hydrogen;

b) alkyl of 1 to 4 carbon atoms, inclusive;

c) alkoxy of 1 to 4 carbon atoms, inclusive;

d) halogen; or e) fluorinated alkyl 1 to 4 carbon atoms, inclusive;
wherein $R^7$ is alkanoyl of 2 to 6 carbon atoms, inclusive; or a pharmaceutically acceptable acid addition salt thereof; or a pharmaceutically acceptable base addition salt thereof.

28. A compound according to claim 27, which is N-[2-[(1H-benzimidazol-2-ylsulfinyl)methyl]phenyl]acetamide.

29. A pharmaceutical composition useful for testing ulcers in mammals comprising a pharmaceutically effective amount of at least one compound according to claim 1, together with one or more non-toxic pharmaceutically acceptable carriers.

30. A pharmaceutical composition according to claim 29 wherein said compound is selected from the group consisting of:

2-[(1H-benzimidazol-2-ylsulfinyl)methyl]benzenamine,

2-[(1H-benzimidazol-2-ylsulfinyl)methyl]-4-chlorobenzenamine,

2-[(1H-benzimidazol-2-ylsulfinyl)methyl]-5-chlorobenzenamine,

2-[(1H-benzimidazol-2-ylsulfinyl)methyl]-4-methoxybenzenamine,

2-[(1H-benzimidazol-2-ylsulfinyl)methyl]-6-methoxybenzenamine,

2-[(1H-benzimidazol-2-ylsulfinyl)methyl]-3-methylbenzenamine,

2-[(1H-benzimidazol-2-ylsulfinyl)methyl]-4-methylbenzenamine,

2-[(1H-benzimidazol-2-ylsulfinyl)methyl]-6-methylbenzenamine,

2-[(1H-benzimidazol-2-ylsulfinyl)methyl]-4-ethylbenzenamine,

2-[(1H-benzimidazol-2-ylsulfinyl)methyl]-6-ethylbenzenamine,

2-[(1H-benzimidazol-2-ylsulfinyl)methyl]-4,6-dimethylbenzenamine,

2-[(1H-benzimidazol-2-ylsulfinyl)methyl]-5-methoxy-4,6-dimethylbenzenamine,

2-[[(4-methyl-1H-benzimidazol-2-yl)sulfinyl]methyl]
benzenamine,
2-[[(5-methoxy-1H-benzimidazol-2-yl)sulfinyl]methyl]
benzenamine,
2-[[(5-methoxy-1H-benzimidazol-2-yl)sulfinyl]methyl]-4-methylbenzenamine,
2-[[(5-methoxy-1H-benzimidazol-2-yl)sulfinyl]methyl]-6-methylbenzenamine,
2-[[(5,6-dimethyl-1H-benzimidazol-2-yl)sulfinyl]methyl]benzenamine,
methyl 2-[[(2-aminophenyl)methyl]sulfinyl]-5-methoxy-1H-benzimidazole-6-carboxylate,
2-[(1H-benzimidazol-2-ylsulfinyl)methyl]-N-methylbenzenamine,
2-[(1H-benzimidazol-2-ylsulfinyl)methyl]-N,N-dimethylbenzenamine,
N-[2-[(1H-benzimidazol-2-ylsulfinyl)methyl]phenyl]
acetamide, or a pharmaceutically acceptable acid addition salt thereof, or a pharmaceutically acceptable base addition salt thereof.

31. A method for treating ulcers in mammals comprising administering a therapeutically effective amount of at least one compound of claim 1 to a mammal in need of such treatment.

32. A method according to claim 31 wherein said compound is selected from the group consisting of:

2-[(1H-benzimidazol-2-ylsulfinyl)methyl]benzenamine,
2-[(1H-benzimidazol-2-ylsulfinyl)methyl]-4-chlorobenzenamine,
2-[(1H-benzimidazol-2-ylsulfinyl)methyl]-5-chlorobenzenamine,
2-[(1H-benzimidazol-2-ylsulfinyl)methyl]-4-methoxybenzenamine,
2-[(1H-benzimidazol-2-ylsulfinyl)methyl]-6-methoxybenzenamine,
2-[(1H-benzimidazol-2-ylsulfinyl)methyl]-3-methylbenzenamine,
2-[(1H-benzimidazol-2-ylsulfinyl)methyl]-4-methylbenzenamine,
2-[(1H-benzimidazol-2-ylsulfinyl)methyl]-6-methylbenzenamine,
2-[(1H-benzimidazol-2-ylsulfinyl)methyl]-4-ethylbenzenamine,
2-[(1H-benzimidazol-2-ylsulfinyl)methyl]-6-ethylbenzenamine,
2-[(1H-benzimidazol-2-ylsulfinyl)methyl]-4,6-dimethylbenzenamine,
2-[(1H-benzimidazol-2-ylsulfinyl)methyl]-5-methoxy-4,6-dimethylbenzenamine,
2-[[(4-methyl-1H-benzimidazol-2-yl)sulfinyl]methyl]
benzenamine,
2-[[(5-methoxy-1H-benzimidazol-2-yl)sulfinyl]methyl]
benzenamine,
2-[[(5-methoxy-1H-benzimidazol-2-yl)sulfinyl]methyl]-4-methylbenzenamine,
2-[[(5-methoxy-1H-benzimidazol-2-yl)sulfinyl]methyl]-6-methylbenzenamine,
2-[[(5,6-dimethyl-1H-benzimidazol-2-yl)sulfinyl]methyl]benzenamine,
methyl 2-[[(2-aminophenyl)methyl]sulfinyl]-5-methoxy-1H-benzimidazole-6-carboxylate,
2-[(1H-benzimidazol-2-ylsulfinyl)methyl]-N-methylbenzenamine,
2-[(1H-benzimidazol-2-ylsulfinyl)methyl]-N,N-dimethylbenzenamine,
N-[2-[(1H-benzimidazol-2-ylsulfinyl)methyl]phenyl]
acetamide, or a pharmaceutically acceptable acid addition salt thereof, or a pharmaceutically acceptable base addition salt thereof.

33. A method for treating ulcers in mammals comprising administering a therapeutically effective amount of a pharmaceutical composition of claim 29 to a mammal in need of such treatment.

* * * * *